(12) United States Patent
Park

(10) Patent No.: US 10,034,616 B2
(45) Date of Patent: Jul. 31, 2018

(54) METHOD AND APPARATUS FOR MEASURING BIOSIGNAL

(71) Applicant: Ji Man Park, Daejeon (KR)

(72) Inventor: Ji Man Park, Daejeon (KR)

( * ) Notice: Subject to any disclaimer, the term of this patent is extended or adjusted under 35 U.S.C. 154(b) by 3 days.

(21) Appl. No.: 15/431,146

(22) Filed: Feb. 13, 2017

(65) Prior Publication Data

US 2018/0035907 A1 Feb. 8, 2018

(30) Foreign Application Priority Data

Aug. 8, 2016 (KR) .................. 10-2016-0100767

(51) Int. Cl.
*A61B 5/04* (2006.01)
*A61B 5/0245* (2006.01)
*A61B 5/0402* (2006.01)
*A61B 5/00* (2006.01)
*H03K 3/0233* (2006.01)

(52) U.S. Cl.
CPC ........ *A61B 5/04012* (2013.01); *A61B 5/0245* (2013.01); *A61B 5/0402* (2013.01); *A61B 5/7203* (2013.01); *A61B 5/7278* (2013.01); *H03K 3/02337* (2013.01)

(58) Field of Classification Search
None
See application file for complete search history.

(56) References Cited

U.S. PATENT DOCUMENTS

| 4,967,108 | A | * | 10/1990 | Lee | ................... | H04W 52/0229 |
| | | | | | | 327/557 |
| 5,716,381 | A | * | 2/1998 | Reggiardo | ........... | A61N 1/3937 |
| | | | | | | 607/5 |
| 9,625,414 | B2 | * | 4/2017 | Yang | ..................... | G01R 35/00 |
| 2013/0237864 | A1 | * | 9/2013 | Mazar | ................. | A61B 5/0215 |
| | | | | | | 600/488 |

* cited by examiner

*Primary Examiner* — Brian T Gedeon
(74) *Attorney, Agent, or Firm* — Novick, Kim & Lee PLLC; Sang Ho Lee

(57) ABSTRACT

Provided is a method and apparatus for measuring a biosignal. The biosignal measurement method may include measuring, at a biosignal measurement apparatus, a biosignal using a biosignal measurement sensor; processing, at the biosignal measurement apparatus, the biosignal and converting the biosignal to a pulse signal using a first voltage distribution time constant circuit and a waveform converter; and counting, at the biosignal measurement apparatus, the pulse signal using a counter and generating first biometric information. The first voltage distribution time constant circuit may filter a signal of a specific frequency band from the biosignal based on voltage distribution using a series resistance included in the first voltage distribution time constant circuit.

12 Claims, 17 Drawing Sheets

METHOD AND APPARATUS FOR MEASURING BIOSIGNAL

CROSS-REFERENCE TO RELATED APPLICATION

This application claims the priority benefit of Korean Patent Application No. 10-2016-0100767 filed on Aug. 8, 2016, in the Korean Intellectual Property Office, the disclosure of which is incorporated herein by reference.

BACKGROUND

1. Field of the Invention

At least one example embodiment relates to a method and apparatus for measuring a signal, and more particularly, to a method and apparatus for measuring a biosignal.

2. Related Art

With the advancement in an economic level and medical technology, individuals' interest on their health is also further increasing. In addition, the proportion of elderly population in Korea exceeded 7% in 2001, and Korea has entered an aging society and the elderly population to be burdened by the society is on the rapid increase. To satisfy such interest on health and reduce medical expenses, a U-heath care system that introduces the ubiquitous concept to a personal health management is proposed as a solution.

U-health care refers to a system that provides a medical service without restriction on a time and space by expanding information, wireless communication technology, and network infrastructure in a medical system. To construct the U-health care system free from time and space constraints, a portable device capable of continuously measuring biosignals needs to be developed.

An existing electrocardiography (ECG) sensor has difficulty in measuring a heart rate from clothes or clothing. For example, if a person shows a great movement, noise becomes serious in an input biosignal and thus, the biosignal becomes unreliable. That is, if a contact portion with the skin surface of a body is unstable, for example, not in close contact, and a movement of a person increases, noise increases in the input biosignal. Due to such noise, it is difficult to perform accurate sensing using the ECG sensor.

SUMMARY

An aspect of at least one example embodiment provides a method of further accurately measuring a biosignal.

Another aspect of at least one example embodiment provides an apparatus for performing a method of further accurately measuring a biosignal.

According to an aspect of at least one example embodiment, there is provided a method of measuring a biosignal, the method including measuring, at a biosignal measurement apparatus, a biosignal using a biosignal measurement sensor, processing, at the biosignal measurement apparatus, the biosignal and converting the biosignal to a pulse signal using a first voltage distribution time constant circuit and a waveform converter, and counting, at the biosignal measurement apparatus, the pulse signal using a counter and generating first biometric information. The first voltage distribution time constant circuit filters a signal of a specific frequency band from the biosignal based on voltage distribution using a series resistance included in the first voltage distribution time constant circuit.

The converting of the biosignal to the pulse signal may include generating, at the biosignal measurement apparatus, the biosignal as a first wave signal using the first voltage distribution time constant circuit and converting, at the biosignal measurement apparatus, the first wave signal to the pulse signal using the waveform converter. The first voltage distribution time constant circuit may include a first series resistance and a second series resistance provided between a power voltage and a ground and configured to distribute the power voltage, and a first capacitor connected between the first series resistance and the second series resistance. The first voltage distribution time constant circuit may have a voltage distribution time constant of a first threshold or less that is determined using the first series resistance, the second series resistance, and the first capacitor. The first voltage distribution time constant circuit may be configured to allow a specific frequency to pass based on a resistance value and a capacitor value, and may serve as a high frequency filter.

Also, the converting of the biosignal to the pulse signal may include generating, at the biosignal measurement apparatus, the biosignal as a first wave signal using the first voltage distribution time constant circuit, filtering, at the biosignal measurement apparatus, and/or amplifying the first wave signal using a filter-and-amplifier, and acquiring the filtered first wave signal, and converting, at the biosignal measurement apparatus, the filtered first wave signal to the pulse signal using the waveform converter. The first voltage distribution time constant circuit may include a first series resistance and a second series resistance provided between a power voltage and a ground and configured to distribute the power voltage, and a first capacitor connected between the first series resistance and the second series resistance. The first voltage distribution time constant circuit may have a voltage distribution time constant of a first threshold or less that is determined using the first series resistance, the second series resistance, and the first capacitor.

Also, the biosignal measurement method may further include generating, at the biosignal measurement apparatus, the biosignal as a second wave signal using a second voltage distribution time constant circuit, converting, at the biosignal measurement apparatus, the second wave signal to a digital signal using an analog-to-digital converter (ADC), and generating, at the biosignal measurement apparatus, second biometric information based on the digital signal.

Also, the first voltage distribution time constant circuit may include a first series resistance and a second series resistance provided between a first power voltage and a ground and configured to distribute the first power voltage, and a first capacitor connected between the first series resistance and the second series resistance. The first voltage distribution time constant circuit may have a voltage distribution time constant of a first threshold or less that is determined using the first series resistance, the second series resistance, and the first capacitor, and the second voltage distribution time constant circuit may include a third series resistance and a fourth series resistance provided between a second power voltage and a ground, and configured to distribute the second power voltage, and a second capacitor connected between the third series resistance and the fourth series resistance. The second voltage distribution time constant circuit may have a voltage distribution time constant of a second threshold or more that is determined using the third series resistance, the fourth series resistance, and the second capacitor.

Also, the biosignal measurement method may further include removing, at the biosignal measurement apparatus, noise in the pulse signal based on a characteristic of the pulse signal, determining, at the biosignal measurement apparatus, a reliability of the biometric information based on comparison between a measurement estimate that is estimated based on previously generated biometric information and the biometric information, and applying, at the biosignal measurement apparatus, the measurement estimate or the biometric information to generate body state information of a measurement target based on the reliability.

According to another aspect of at least one example embodiment, there is provided a biosignal measurement apparatus including a processor. The processor is configured to measure a biosignal using a biosignal measurement sensor, to process the biosignal and convert the biosignal to a pulse signal using a first voltage distribution time constant circuit and a waveform converter, and to count the pulse signal using a counter and generate first biometric information. The first voltage distribution time constant circuit filters a signal of a specific frequency band from the biosignal based on voltage distribution using a series resistance included in the first voltage distribution time constant circuit.

The processor may be configured to generate the biosignal as a first wave signal using the first voltage distribution time constant circuit and to convert the first wave signal to the pulse signal using the waveform converter. The first voltage distribution time constant circuit may include a first series resistance and a second series resistance provided between a power voltage and a ground and configured to distribute the power voltage, and a first capacitor connected between the first series resistance and the second series resistance. The first voltage distribution time constant circuit may have a voltage distribution time constant of a first threshold or less that is determined using the first series resistance, the second series resistance, and the first capacitor.

Also, the processor may be configured to generate the biosignal as a first wave signal using the first voltage distribution time constant circuit, to filter and/or amplify the first wave signal using a filter-and-amplifier, and acquire the filtered first wave signal, and to convert the filtered first wave signal to the pulse signal using the waveform converter. The first voltage distribution time constant circuit may include a first series resistance and a second series resistance provided between a power voltage and a ground and configured to distribute the power voltage, and a first capacitor connected between the first series resistance and the second series resistance. The first voltage distribution time constant circuit may have a voltage distribution time constant of a first threshold or less that is determined using the first series resistance, the second series resistance, and the first capacitor.

Also, the processor may be configured to generate the biosignal as a second wave signal using a second voltage distribution time constant circuit, to convert the second wave signal to a digital signal using an ADC, and to generate second biometric information based on the digital signal.

Also, the first voltage distribution time constant circuit may include a first series resistance and a second series resistance provided between a first power voltage and a ground and configured to distribute the first power voltage, and a first capacitor connected between the first series resistance and the second series resistance. The first voltage distribution time constant circuit may have a voltage distribution time constant of a first threshold or less that is determined using the first series resistance, the second series resistance, and the first capacitor, and the second voltage distribution time constant circuit may include a third series resistance and a fourth series resistance provided between a second power voltage and a ground, and configured to distribute the second power voltage, and a second capacitor connected between the third series resistance and the fourth series resistance. The second voltage distribution time constant circuit may have a voltage distribution time constant of a second threshold or more that is determined using the third series resistance, the fourth series resistance, and the second capacitor.

Also, the processor may be configured to remove noise in the pulse signal based on a characteristic of the pulse signal, to determine reliability of the biometric information based on comparison between a measurement estimate that is estimated based on previously generated biometric information and the biometric information, and to apply the measurement estimate or the biometric information to generate body state information of a measurement target based on the reliability.

According to example embodiments, a biosignal measurement method and apparatus may acquire further accurate biometric information of a measurement target by removing noise in an input biosignal using a voltage distribution time constant circuit and by converting the biosignal to a pulse signal using a waveform converter.

Other features and aspects will be apparent from the following detailed description, the drawings, and the claims.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1:
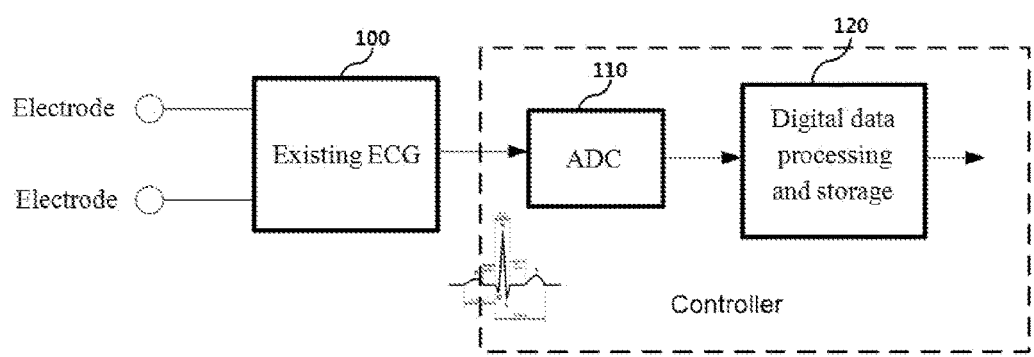
FIG. 1 is a diagram illustrating a method of measuring a heart rate and detecting an electrocardiography (ECG) waveform using an existing ECG sensor.

Hereinafter, example embodiments will be described with reference to the accompanying drawings. Herein, thicknesses of lines, sizes of constituent elements, etc., illustrated in the drawings, may be exaggerated for clarity and convenience of description.

Further, terms described in the following are ones defined based on functions in the present disclosure and thus, may vary based on the intent of a user or an operator, or custom. Accordingly, the definition of such terms should be made based on the overall description disclosed in the present specification.

The features described herein may be embodied in different forms, and are not to be construed as being limited to the example embodiments described herein. Rather, the example embodiments described herein have been provided so that this disclosure will be thorough and complete, and will convey the full scope of the disclosure to one of ordinary skill in the art.

The following structural or functional descriptions are exemplary to merely describe the example embodiments, and the scope of the example embodiments is not limited to the descriptions provided in the present specification. Various changes and modifications can be made thereto by those of ordinary skill in the art.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

It will be understood that when a component is referred to as being "connected to" another component, the component can be directly connected or coupled to the other component or intervening components may be present.

As used herein, the singular forms are intended to include the plural forms as well, unless the context clearly indicates otherwise. It should be further understood that the terms "comprises/includes" and/or "comprising/including," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching with contextual meanings in the related art and are not to be construed as an ideal or excessively formal meaning unless otherwise defined herein.

When it is determined discussions related to a related known operation or configuration that may make the purpose of the example embodiments unnecessarily ambiguous in describing the example embodiments, such discussions in the detailed description will be omitted here.

Example embodiments refer to the accompanying drawings illustrated as examples of the disclosure. The example embodiments are explained to be readily carried out by one of ordinary skill in the art. It should be understood that various example embodiments may differ from each other, however, may not need to be exclusive with respect to each other. For example, specific shapes, structures, and characteristics disclosed herein may be embodied through other example embodiments without departing from the spirit and scope of the disclosure. Further, it should be understood that locations or arrangements of the individual constituent elements disclosed herein may be modified without departing from the spirit and scope of the disclosure. Accordingly, the following description is not construed to be limiting and, if appropriately described, the scope of the disclosure may be limited by the claims and their equivalents. Like reference numerals illustrated in the drawing refer to like functions throughout.

Hereinafter, the example embodiments will be described with reference to the accompanying drawings.

FIG. 1 is a diagram illustrating a method of measuring a heart rate and detecting an electrocardiography (ECG) waveform using an existing ECG sensor.

Referring to FIG. 1, a biosignal measured using an existing ECG sensor 100 may not have a high accuracy.

An existing biosignal measurement apparatus may acquire biometric information of a measurement target by performing signal processing on a biosignal sensed at the ECG sensor 100, using an analog-to-digital converter (ADC) 110 and a digital data processing and storage 120.

When measuring a biosignal using the existing biosignal measurement apparatus, the measurement target, for example, a person, may move greatly. In this case, serious noise may be included in an input biosignal. Accordingly, it may be difficult to accurately measure heart rate data.

Alternatively, due to a not-close contact between the skin surface of the measurement target and the ECG sensor 100 and an increase in a movement of the measurement target, etc., noise by another biosignal may increase. In this case, noise may enter an ECG contact point and may make it difficult to measure a biosignal of the measurement target. Also, noise by clothing, another element such as static, etc., may be sensed as a biosignal at the ECG sensor 100. Thus, it may be difficult to measure an accurate biosignal.

Hereinafter, a method of further accurately measuring a biosignal of a measurement target using a sensor according to an example embodiment will be described.

Herein, disclosed are a method of generating biometric information, for example, heart beat information and ECG information, based on a biosignal at a biosignal measurement apparatus using an ECG sensor or a biosignal measurer, and a method of generating biometric information, for example, pulse rate information and pulse waveform information, based on a biosignal at a biosignal measurement apparatus using a photo-plethysmography (PPG) sensor or a biosignal measurer. Body state information, for example, a stress index, blood pressure, etc., of the measurement target may be generated based on the generated biometric information. The body state information may be used as information to monitor a state of the measurement target. If a manager of the measurement target is present, the body state information of the measurement target may be transferred to the manager.

As described above, a biosignal sensing result of the existing biosignal measurement apparatus using an existing biosignal sensor, for example, an ECG sensor, a PPG sensor, etc., according to the related art may be reliable only when the measurement target is in a static state. Conversely, when the measurement target is in a dynamic state, the existing biosignal measurement apparatus may have an unreliable sensing value.

A biosignal measurement method and apparatus according to an example embodiment may provide a biosignal processing method for generating highly reliable biometric information.

Although the measurement target is in a dynamic state, the biosignal measurement apparatus according to an example embodiment may generate further highly reliable biometric information, such as a heart rate, a pulse, etc., based on a circuit configuration of a new sensor signal processing apparatus and a biosignal analysis algorithm. Further accurate and reliable biosignals, for example, a heart rate, a pulse, etc., may be acquired through two stages; a primary stage of performing a biosignal stabilization using the signal processing apparatus and a secondary stage of applying a biosignal analysis algorithm to a biosignal received from the signal processing apparatus.

Hereinafter, a method and apparatus for further accurately measuring a biosignal of a measurement target using a sensor according to an example embodiment will be described. A biosignal measurement apparatus according to an example embodiment may be configured as a plurality of individual devices, for example, chips, or a single chip.

Figure 2A:
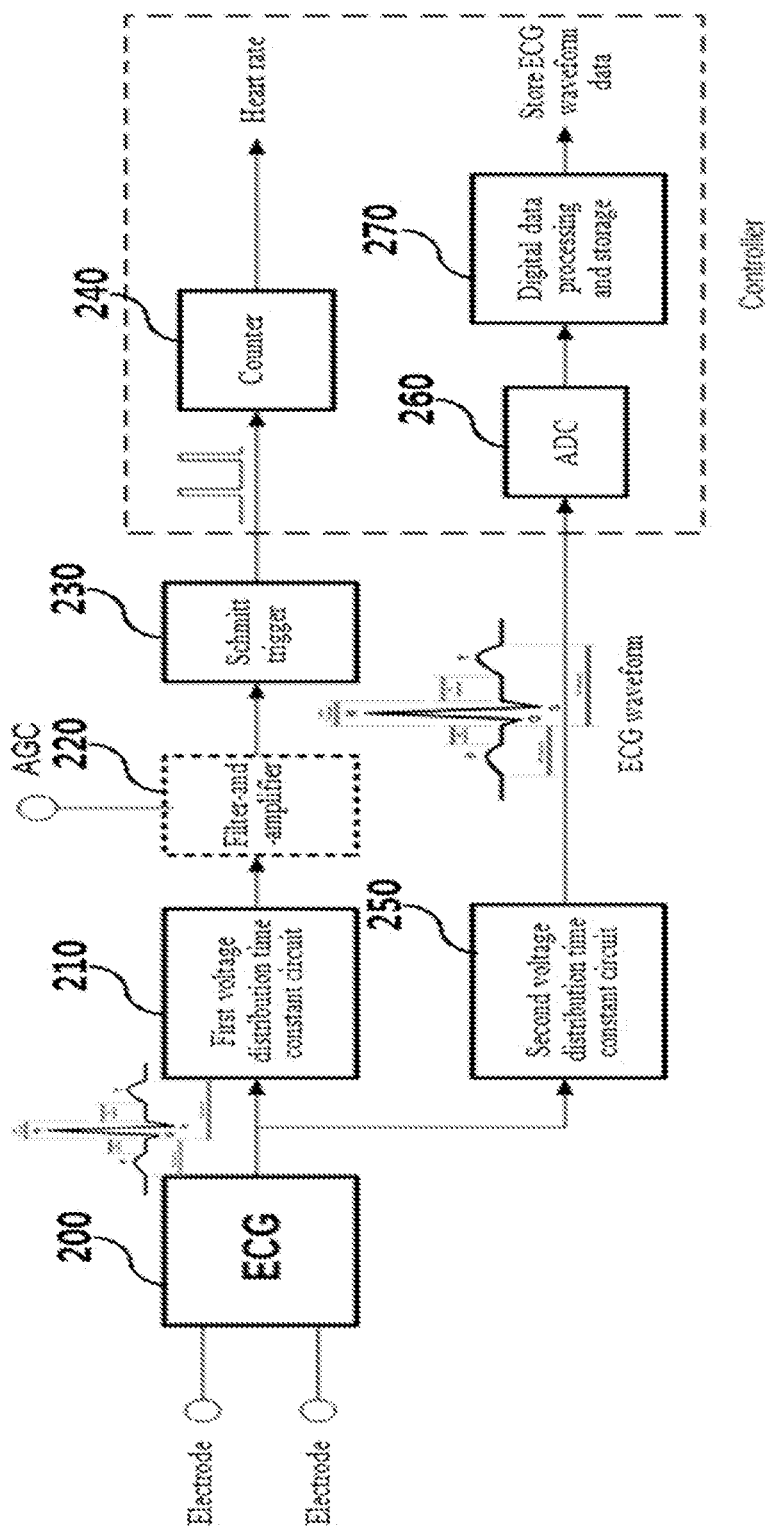
FIGS. 2A and 2B illustrate examples of a biosignal measurement apparatus for measuring a biosignal of a measurement target according to an example embodiment.
Figure 2B:
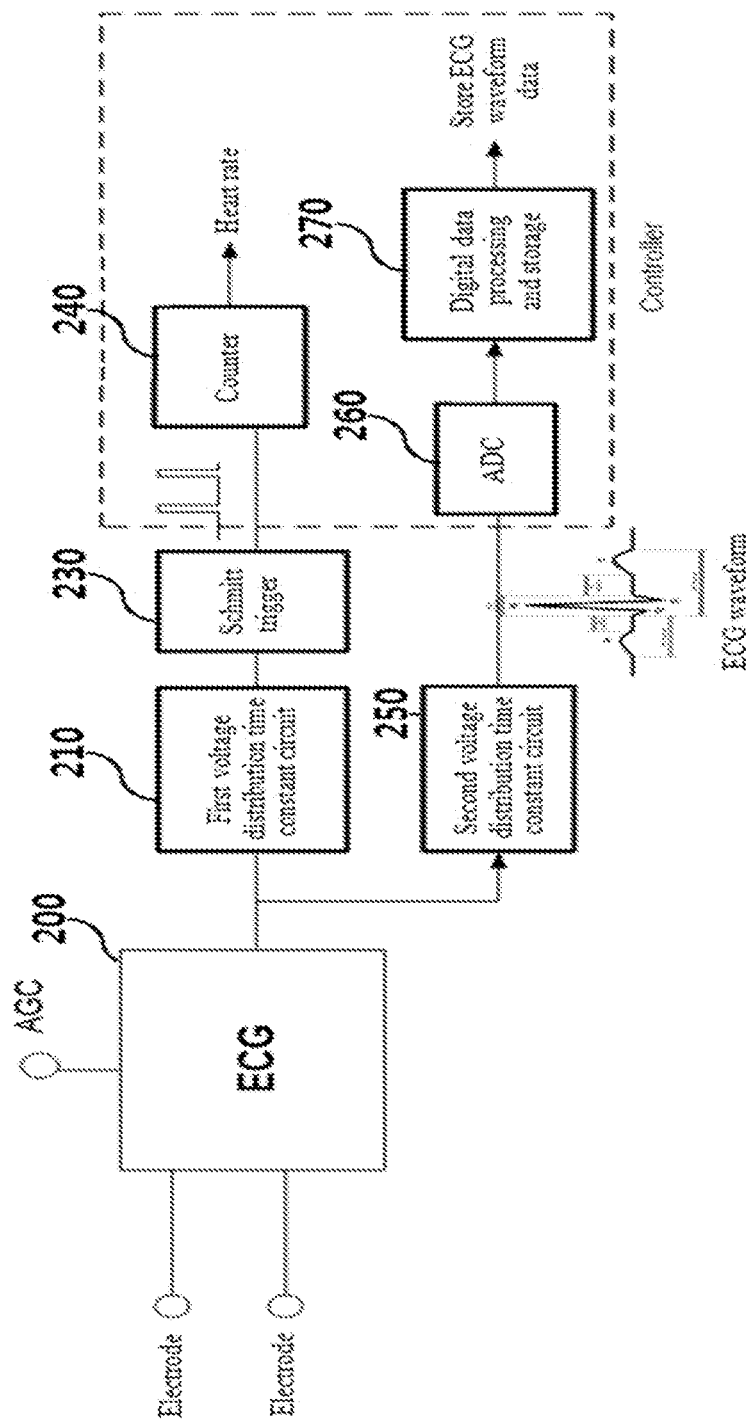

FIGS. 2A and 2B illustrate examples of a biosignal measurement apparatus for measuring a biosignal of a measurement target according to an example embodiment.

FIGS. 2A and 2B illustrate examples of a biosignal measurement apparatus for generating biometric information, for example, heart rate information and ECG information, using an ECG sensor.

The biosignal measurement apparatus may include a heart rate measurer configured to measure a heart rate of a measurement target and an ECG measurer configured to measure ECG of the measurement target.

Referring to FIG. 2A, an ECG signal that is a biosignal sensed at an ECG sensor 200 may be input to the heart rate measurer and the ECG measurer.

The heart rate measurer may include a first voltage distribution time constant circuit 210, a filter-and-amplifier 220, a Schmitt trigger 230, and a counter 240.

The first voltage distribution time constant circuit 210 may be used to primarily detect an R wave signal having a peak value from the entire ECG periodic waveform included in an ECG signal, based on a first voltage distribution time constant. The R wave signal detected using the first voltage distribution time constant circuit 210 may be used to acquire heart rate information of the measurement target.

The filter-and-amplifier 220 may additionally filter a wave signal of another frequency domain from the R wave signal received from the first voltage distribution time constant circuit 210, and may amplify the R wave signal if a magnitude of the R wave signal is relatively small. The R wave signal filtered and/or filtered at the filter-and-amplifier 220 may be referred to as a "filtered R wave signal".

The filter-and-amplifier 220 may be configured as a separate configuration, for example, a filter and an amplifier that are separate from each other.

FIG. 2B illustrates a heart rate measurer configured to measure a heart rate without using the filter-and-amplifier 220 of FIG. 2A. The filter-and-amplifier 220 is a selective configuration. Thus, if there is no need to filter and/or amplify an R wave signal detected using the first voltage distribution time constant circuit 210, the R wave signal may be immediately input to the Schmitt trigger 230 without going through the filter-and-amplifier 220.

The Schmitt trigger 230 may receive the R wave signal or the filtered R wave signal, and may convert the same to a pulse signal. The Schmitt trigger 230 is an example of a circuit configured to convert a wave signal to a pulse signal, and may employ various types of pulse wave conversion circuits.

The counter 240 may count the pulse signal generated at the Schmitt trigger 230 and may acquire heart rate information. The heart rate measurer may easily measure a heart rate of the measurement target during a preset period of time based on a counting result of the counter 240.

The ECG measurer may include a second voltage distribution time constant circuit 250, an ADC 260, and a digital data processing and storage 270.

The second voltage distribution time constant circuit 250 may be configured to generate ECG information based on an ECG signal that is sensed at the ECG sensor 200 based on a second voltage distribution time constant greater than the first voltage distribution time constant used at the first voltage distribution time constant circuit 210. A signal output through the second voltage distribution time constant circuit 250 may be identical to an ECG signal sensed at the ECG sensor 200. A buffer may be disposed in front of the second voltage distribution time constant circuit 250 for signal processing at the second voltage distribution time constant circuit 250.

A waveform output through the second voltage distribution time constant circuit 250 may be converted to digital data through the ADC 260, and ECG information of the measurement target may be acquired by processing digitalized ECG data. The ECG information generated at the ECG measurer may be used to acquire further detail body state information, for example, a biological index and a physiological index, of the measurement target.

In the ECG measurer, the ADC 260 for converting an analog ECG signal to digital ECG data may be configured using a variety of schemes. For example, the ADC 260 may be a successive approximation register (SAR) ADC, a delta-sigma ADC, a sensor-to-time ADC, and the like. An output of the sensor-to-time ADC may be a value associated with a variation width of a pulse. If the output of the sensor-to-time ADC input to an n-bit counter, an ADC output of n-bit may be acquired. The ADC output may be used to acquire further detail body state information of the measurement target as digital ECG data.

According to an example embodiment, the biosignal measurement apparatus may further include an automatic gain controller (AGC). The AGC may be included in the biosignal measurement apparatus and configured to adjust an output magnitude of a biosignal, for example, an ECG signal, acquired from the measurement target. For example, the AGC may adjust the output magnitude of the biosignal through connection to the amplifier of FIG. 2A and the ECG sensor 200 of FIG. 2B.

A different biosignal may be output for each measurement target. Thus, the AGC may generate a biosignal to have a magnitude greater than or equal to a predetermined threshold. If it is difficult to measure a biosignal due to a significantly large or small waveform based on a threshold magnitude, the AGC may generate a biosignal to have a predetermined magnitude based on the threshold magnitude.

An operation of each configuration of the heart rate measurer and the ECG measurer may be controlled using a processor, for example, a micro controller unit (MCU) of the biosignal measurement apparatus.

Figure 3:
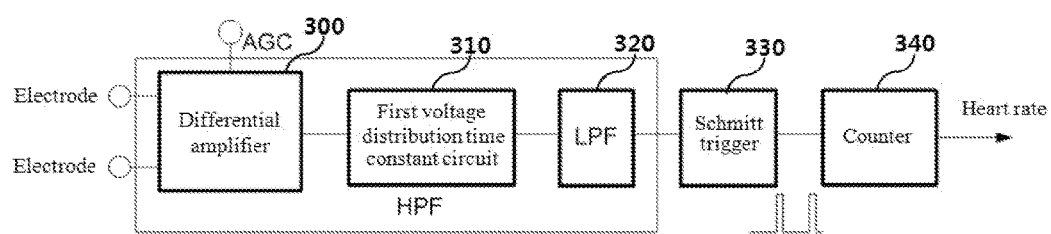
FIG. 3 illustrates an example of a biosignal measurement apparatus for measuring a biosignal of a measurement target according to an example embodiment.

FIG. 3 illustrates an example of a biosignal measurement apparatus for measuring a biosignal of a measurement target according to an example embodiment.

FIG. 3 illustrates a biosignal measurement apparatus using an ECG sensor configured to measure a heart rate.

Referring to FIG. 3, when the biosignal measurement apparatus is to measure only a heart rate using the ECG sensor, only a heart rate measurer may be included in the biosignal measurement apparatus.

The biosignal measurement apparatus may include the ECG sensor, a Schmitt trigger 330, and a counter 340. The ECG sensor may include a differential amplifier 300 configured to amplify signals of two electrodes, a first voltage distribution time constant circuit 310 configured to serve as a high pass filter (HPF), and a low pass filter (LPF) 320.

A biosignal acquired from the measurement target may be amplified, an R wave signal may be amplified through the HPF 310, and a signal of another frequency band aside from the R wave signal may be filtered through the LPF 320. The filtered R wave signal may be converted to a pulse signal through the Schmitt trigger 330, and heart rate information may be acquired by counting the pulse signal using the counter 340. When only a heart rate is to be measured using the biosignal measurement apparatus, a separate ADC and complex algorithm for measuring a heart rate may not be required. According to example embodiments, the biosignal measurement apparatus may acquire heart rate information using a simple circuit configuration and easy counting scheme.

Figure 4:
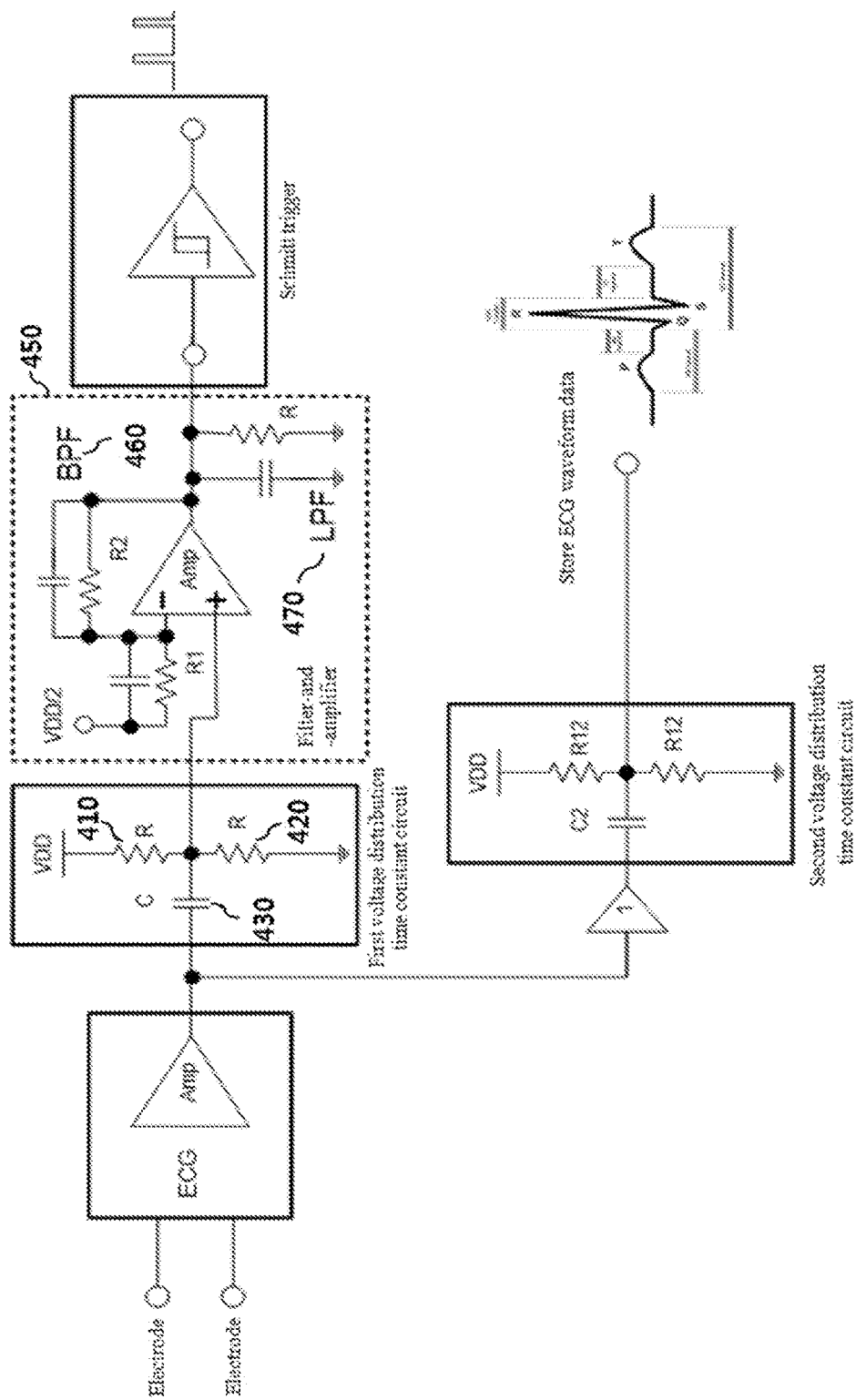
FIGS. 4 through 6 are circuit diagrams illustrating examples of a biosignal measurement apparatus according to an example embodiment.
Figure 5:
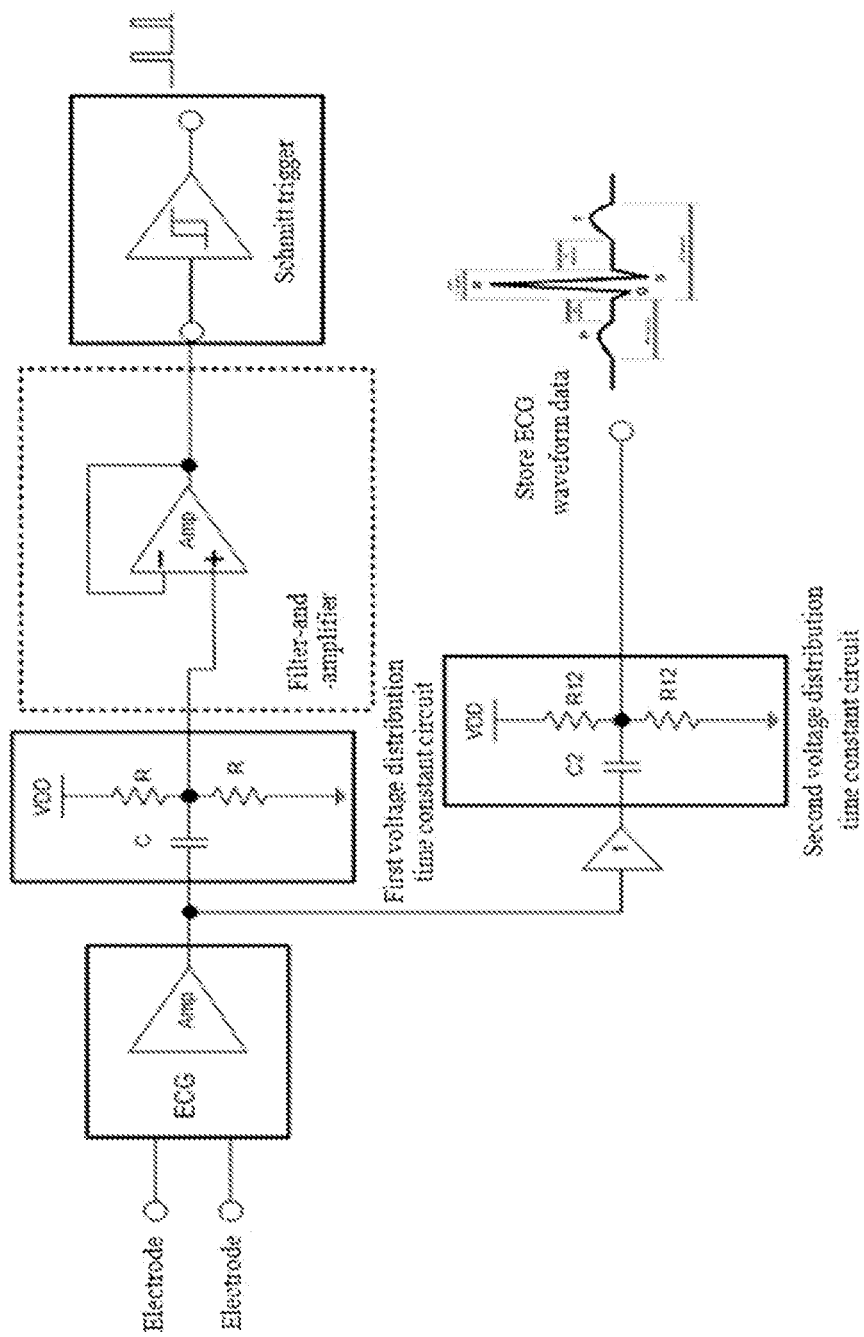
Figure 6:
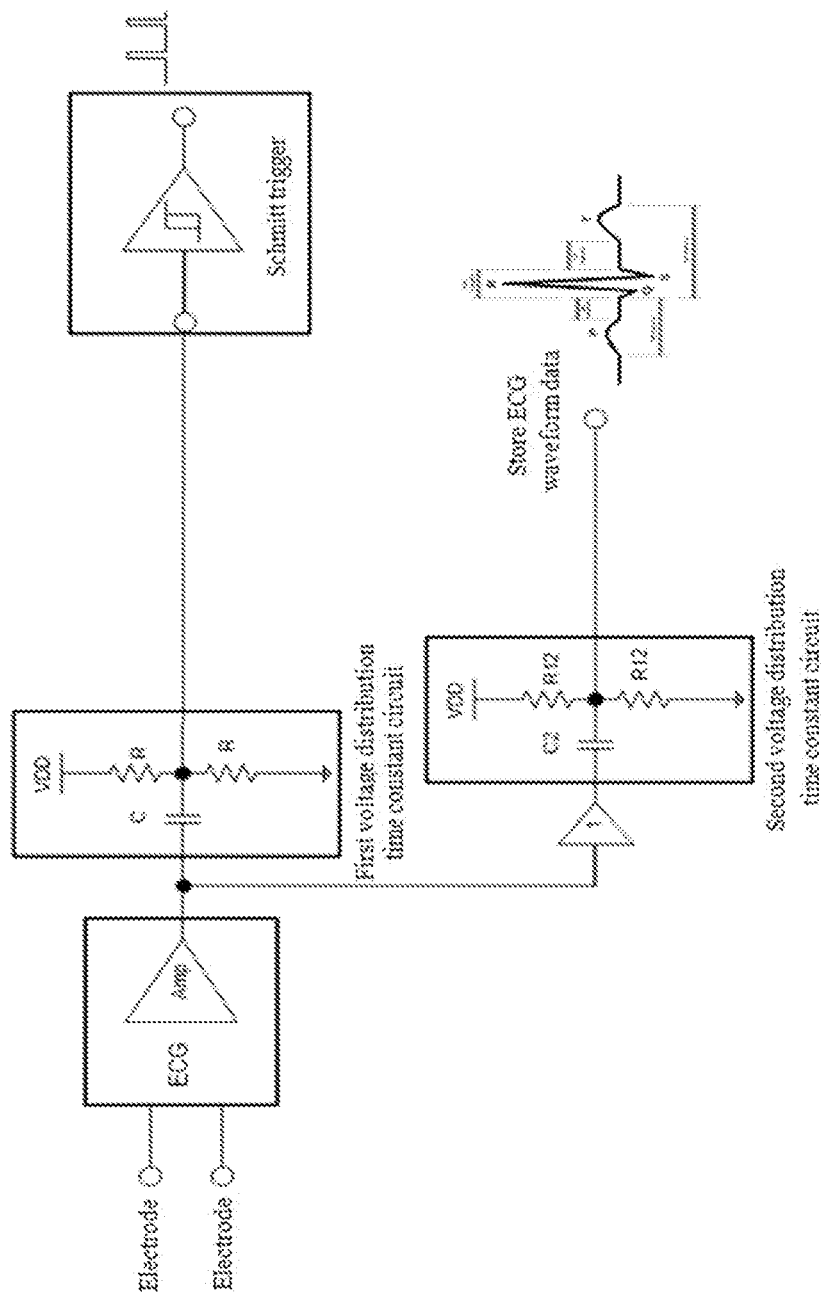

FIGS. 4 through 6 are circuit diagrams illustrating examples of a biosignal measurement apparatus according to an example embodiment.

FIG. 4 illustrates a circuit diagram of a first voltage distribution time constant circuit, a second voltage distribution time constant circuit, and a filter-and-amplifier. For clarity of description, FIG. 4 illustrates a circuit diagram in which a counter is removed from a heart rate measurer and an ADC and a signal processor are removed from an ECG measurer.

Referring to FIG. 4, each of the first voltage distribution time constant circuit and the second voltage distribution time constant circuit may be configured using two series resistances, for example, a first series resistance 410 and a second series resistance 420, connected in series between a power voltage (VDD) and a ground and a capacitor 430 connected between the first series resistance 410 and the second series resistance 420.

The first series resistance 410 and the second series resistance 420 may be configured to distribute the power voltage, and the capacitor 430 may be configured to remove a direct current (DC) component from an ECG output waveform. For example, the two series resistances, for example, the first series resistance 410 and the second series resistance 420, may be metal oxide semiconductor (MOS) resistances.

Voltage distribution time constant may be adjusted based on values of the resistances, for example, the first series resistance 410 and the second series resistance 420, and the capacitor 430.

If the voltage distribution time constant relatively decreases, a high frequency characteristic of a signal output through a voltage distribution time constant circuit may relatively become strong, that is, increase. Accordingly, first voltage distribution time constant of the first voltage distribution time constant circuit may be set to have a relatively low value or a value less than a first threshold, and an R wave signal among ECG signals may be output through the first voltage distribution time constant circuit. A remaining waveform included in the ECG signals sensed at the ECG sensor may correspond to a low frequency and may be removed.

Conversely, if the voltage distribution time constant relatively increases, the high frequency characteristic of the signal output through the voltage distribution time constant circuit may relatively become weak, that is, decrease. The entire ECG signal waveform may be output. Accordingly, second voltage distribution time constant of a second voltage distribution time constant circuit may be set to have a relatively high value or a value greater than a second threshold. The entire ECG signal waveform may be output through the second voltage distribution time constant circuit.

That is, the first voltage distribution time constant circuit may allow an R wave signal to pass and may not allow a remaining signal aside from the R wave signal among ECG signals to pass based on values of resistance and a capacitor. However, the first voltage time constant circuit has a characteristic of allowing a high frequency signal to pass and thus, may allow high frequency noise as well as the R wave signal to pass. The high frequency signal or the high frequency may be filtered out by an filter-and-amplifier 450, as described above. To remove a high frequency signal, the filter-and-amplifier 450 may include at least one of an LPF 470 configured to allow only a signal of a threshold frequency or less to pass and a BPF 460 configured to allow only a signal aside from a signal having a frequency less than a first threshold frequency and a signal having a second threshold frequency or more to pass.

Alternatively, the filter-and-amplifier 450 may be configured using a buffer provided to an input end and a capacitor and a resistance provided to an output end, or using only the capacitor.

The filtered R wave signal that passes the filter-and-amplifier 450 may be input to a Schmitt trigger and may be converted to a pulse signal. A counter may count the pulse signal acquired through the Schmitt trigger and may acquire heart rate information.

FIG. 5 illustrates an example of a biosignal measurement apparatus that includes only an amplifier instead of including a filter in the example of FIG. 4, and FIG. 6 illustrates an example of a biosignal measurement apparatus that does not illustrate a filter and an amplifier in the example of FIG. 4.

Figure 7A:
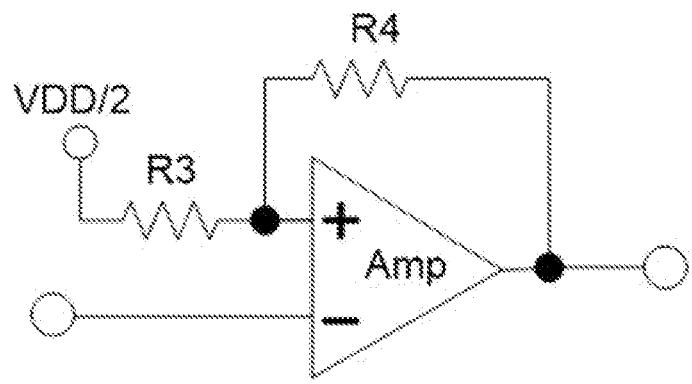
FIGS. 7A and 7B are circuit diagrams illustrating a Schmitt trigger according to an example embodiment.
Figure 7B:
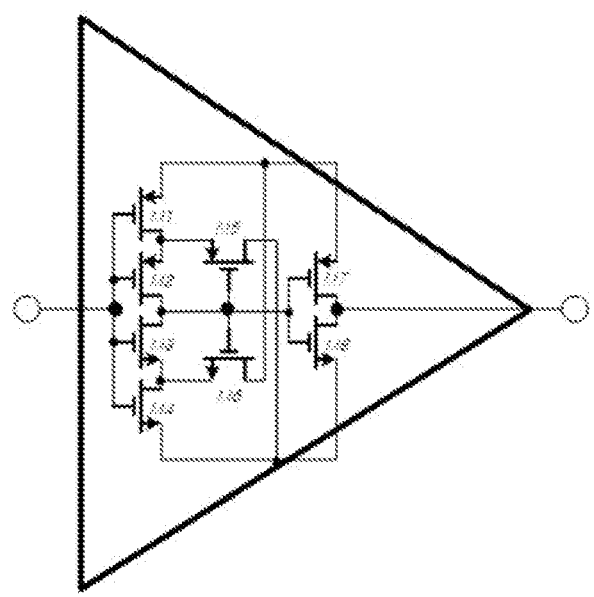

FIGS. 7A and 7B are circuit diagrams illustrating a Schmitt trigger according to an example embodiment.

FIGS. 7A and 7B illustrate examples of a Schmitt trigger configured to convert an amplified R wave signal or an R wave signal to a pulse signal. Hereinafter, although an input signal is assumed as a filtered R wave signal for clarity of description, the input signal may be an R wave signal having not passed through a filter-and-amplifier.

FIG. 7A illustrates a Schmitt trigger circuit configured based on an operational amplifier and FIG. 7B illustrates a digital Schmitt trigger circuit configured based on a complementary metal-oxide semiconductor (CMOS).

According to an example embodiment, among Schmitt trigger circuits configured to convert an amplified R wave signal to a pulse signal, the Schmitt trigger circuit configured based on the operational amplifier may determine a level of threshold voltage based on a resistance value, may output 1 if the amplified R wave signal reaches a relatively high threshold voltage VTH, and may output 0 if the amplified R wave signal reaches a relatively low threshold voltage VTL.

The digital Schmitt trigger circuit configured based on the CMOS may determine a level of threshold voltage based on a width/length (W/L) ratio of the CMOS. Similarly, the digital Schmitt trigger circuit configured based on the CMOS may output 1 if the amplified R wave signal reaches a relatively high threshold voltage VTH, and may output 0 if the amplified R wave signal reaches a relatively low threshold voltage VTL.

Figure 8A:
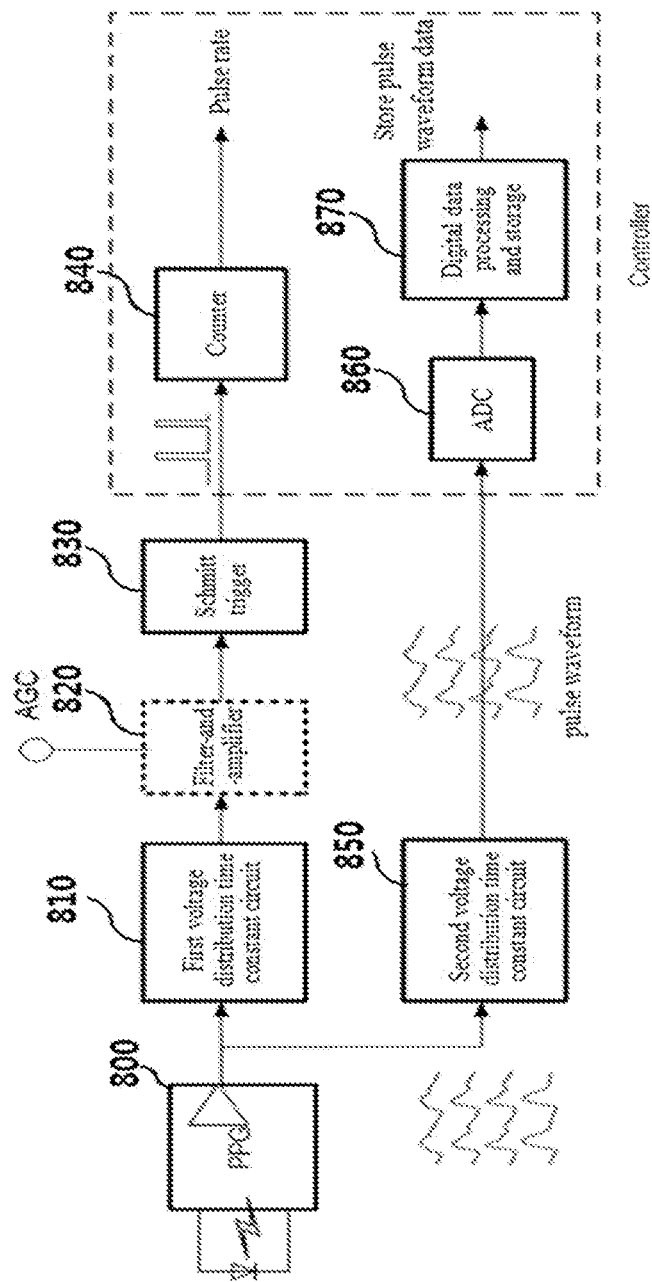
FIGS. 8A, 8B, and 8C illustrate examples of a biosignal measurement apparatus for measuring a biosignal of a measurement target according to an example embodiment.
Figure 8B:
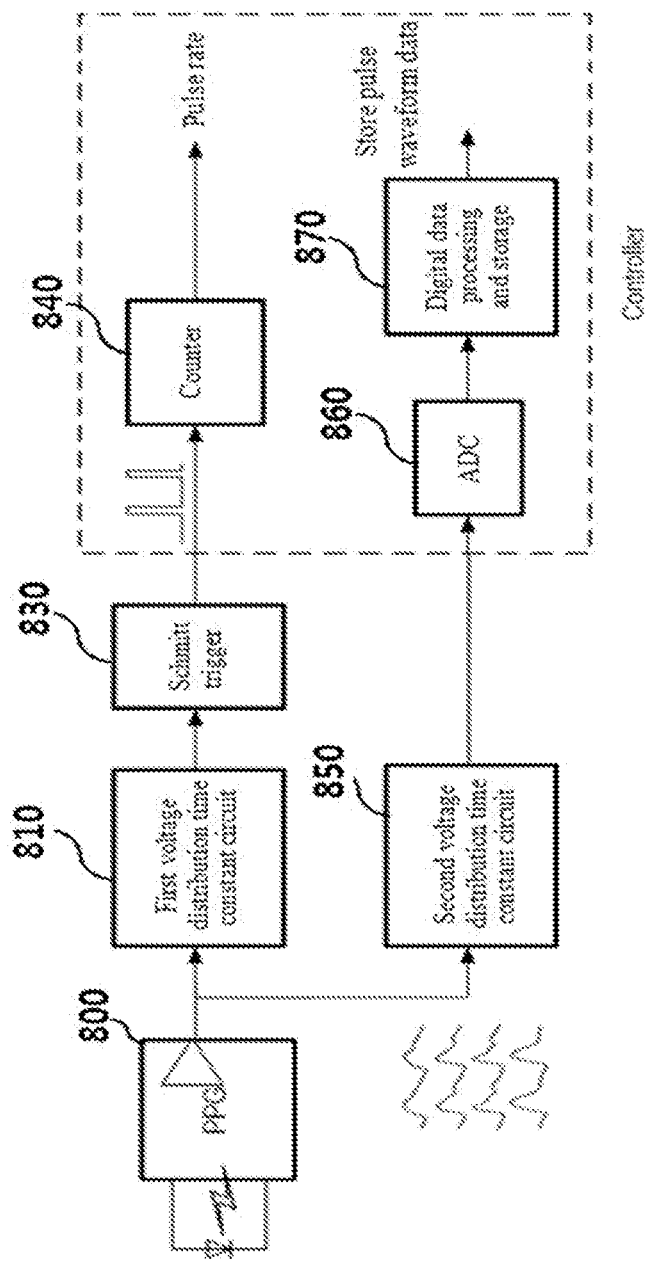
Figure 8C:
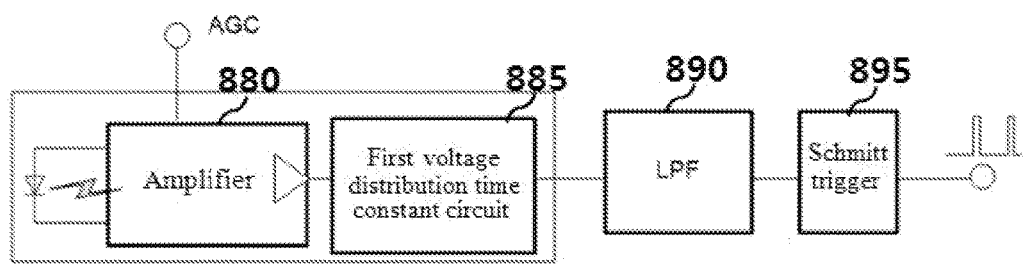

FIGS. 8A, 8B, and 8C illustrate examples of a biosignal measurement apparatus for measuring a biosignal of a measurement target according to an example embodiment.

FIGS. 8A, 8B, and 8C illustrate examples of a biosignal measurement apparatus for generating pulse rate information and pulse waveform information using a PPG sensor according to an example embodiment.

Referring to FIGS. 8A and 8B, similar to a biosignal measurement apparatus configured based on an ECG sensor, a biosignal measurement apparatus configured based on a PPG sensor 800 may measure a pulse rate of a measurement target, and may acquire pulse rate information and may also acquire pulse waveform information. A pulse wave signal that is an analog signal may be input to a first voltage distribution time constant circuit 810, and the pulse wave signal that passes through the first voltage distribution time constant circuit 810 may be stabilized using a capacitor included in the first voltage distribution time constant circuit 810. Only a frequency waveform of a predetermined frequency band among pulse wave signals may be output based on a voltage distribution time constant of the first voltage distribution time constant circuit 810.

Referring to FIG. 8A, a primary filtering pulse wave signal that is primarily filtered using the first voltage distribution time constant circuit 810 may be input to a Schmitt trigger 830 through an additional filter-and-amplifier 820 for removing noise. The primary filtering pulse wave signal having gone through the additional filter-and-amplifier 820, which is input to the Schmitt trigger 830, may be referred as a secondary filtering pulse wave signal. Alternatively, referring to FIG. 8B, the primary filtering pulse wave signal may be immediately input to the Schmitt trigger 830.

The Schmitt trigger 830 may output the primary filtering pulse wave signal or the secondary filtering pulse wave signal as the pulse signal. The pulse signal may operate as a clock of a counter 840 and may be used to determine pulse rate information.

Also, a pulse wave signal that is an analog signal may be input to a second voltage distribution time constant circuit 850. The second voltage distribution time constant circuit 850 may acquire a signal similar to a pulse wave signal that is an output signal output through the PPG sensor 800, based on a second voltage distribution time constant greater than the first voltage distribution time constant of the first voltage distribution time constant circuit 810. The pulse wave signal output through the second voltage distribution time constant circuit 850 may be converted to a digital signal through an ADC 860. The digitalized pulse wave signal may be processed and stored using a digital data processing and storage 870. Pulse waveform information may be generated based on the signal-processed pulse wave signal.

FIG. 8C illustrates a configuration of a biosignal measurement apparatus for measuring only a pulse rate according to an example embodiment.

Similarly, a biosignal measurement apparatus based on a PPG sensor may include the PPG sensor, an LPF 890, a Schmitt trigger 895, and a counter. The PPG sensor may include an amplifier 880 and a first voltage distribution time constant circuit 885.

That is, a pulse wave signal acquired from a measurement target may be amplified using the amplifier 880 and may be primarily filtered using the first voltage distribution time constant circuit 885 configured to serve as an HPF. The primarily filtered primary filtering pulse wave signal may be transferred to the LPF 890. The LPF 890 may perform secondary filtering of the received signal and may generate a secondary filtering pulse wave signal. Next, the secondary filtering pulse wave signal that is filtered using the HPF and the LPF 890 may be converted to a pulse signal through the Schmitt trigger 895, and the counter may count the pulse signal and may acquire pulse rate information.

According to an example embodiment, a biosignal measurement method may include measure, at a biosignal measurement apparatus, a biosignal, for example, an ECG signal and a pulse wave signal, using a biosignal measurement sensor, processing, at the biosignal measurement apparatus, the biosignal and converting the biosignal to a pulse signal using a first voltage distribution time constant circuit and a waveform converter, and counting, at the biosignal measurement apparatus, the pulse signal using a counter and generating first biometric information, for example, heart rate information and pulse rate information.

The first voltage distribution time constant circuit may filter a signal of a specific frequency band from the biosignal based on voltage distribution using a series resistance included in the first voltage distribution time constant circuit. In detail, the first voltage distribution time constant circuit may include a first series resistance and a second series resistance provided between a power voltage and a ground and configured to distribute the power voltage, and a first capacitor connected between the first series resistance and the second series resistance. The first voltage distribution time constant circuit may have a voltage distribution time constant of a first threshold or less based on the first series resistance, the second series resistance, and the first capacitor.

To generate a pulse signal, the biosignal measurement apparatus may perform operations of generating the biosignal as a first wave signal, for example, an R wave signal and a primary filtering pulse wave signal, using the first voltage distribution time constant circuit, and converting the first wave signal to the pulse signal using a waveform converter, for example, a Schmitt trigger.

Alternatively, to generate a pulse signal, the biosignal measurement apparatus may perform operations of generating the biosignal as the first wave signal using the first voltage distribution time constant circuit, filtering and/or amplifying the first wave signal using a filter-and-amplifier, and acquiring a filtered first wave signal, for example, a filtered R wave signal and a secondary filtering pulse wave signal, and converting the filtered first wave signal to the pulse signal using the waveform converter.

Also, the biosignal measurement apparatus may perform operations of generating the biosignal as a second wave signal, for example, a pseudo ECG signal and a pseudo pulse wave signal, using a second voltage distribution time constant circuit, converting the second wave signal to a digital signal using an ADC, and generating second biometric information based on the digital signal.

The second voltage distribution time constant circuit may include a third series resistance and a fourth series resistance provided between a second power voltage and a ground and configured to distribute the second power voltage, and a second capacitor connected between the third series resistance and the fourth series resistance. The second voltage distribution time constant circuit may have a voltage distribution time constant of a second threshold or more that is determined based on the third series resistance, the fourth series resistance, and the second capacitor.

Also, the biosignal measurement apparatus may remove noise in the pulse signal based on a characteristic of the pulse signal, and may determine a reliability of biometric information based on comparison between a measurement estimate that is estimated based on previously generated biometric information and the biometric information. The measurement estimate or the biometric information may be used to generate body state information of the measurement target based on the reliability.

Figure 9A:
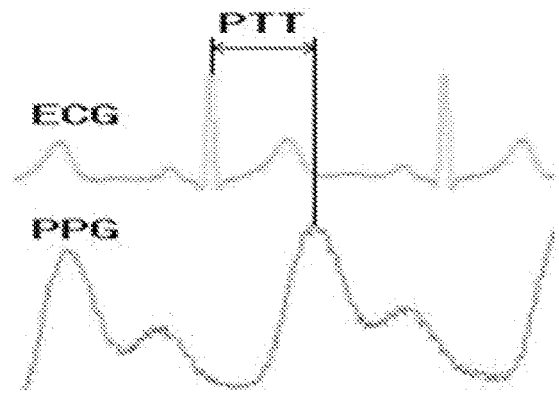
FIGS. 9A and 9B illustrate examples of describing a method of analyzing a biosignal according to an example embodiment.
Figure 9B:
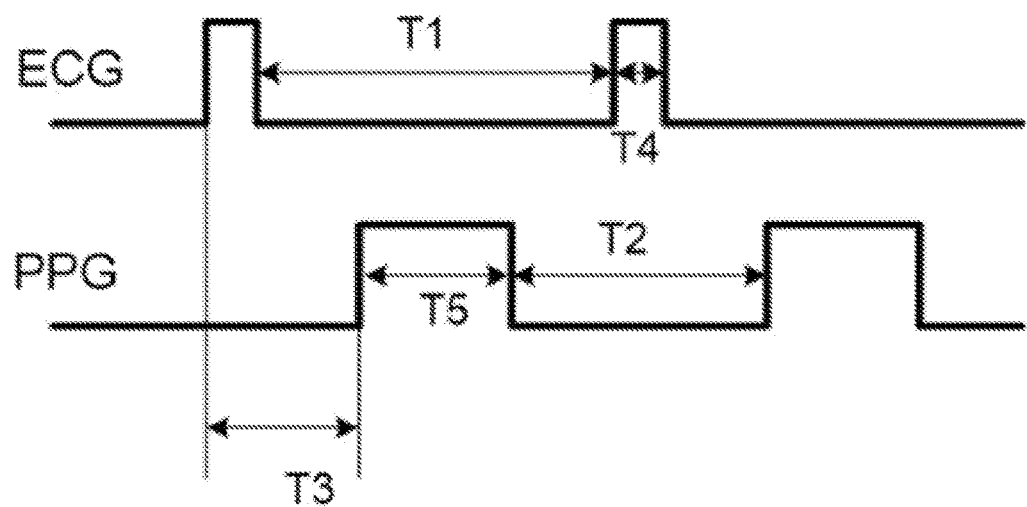

FIGS. 9A and 9B illustrate examples of describing a method of analyzing a biosignal according to an example embodiment.

FIG. 9A illustrates a biosignal output based on an ECG sensor and PPG sensor.

FIG. 9B illustrates an example of converting a biosignal output based on an ECG sensor and a PPG sensor as an output waveform of a biosignal analysis apparatus according to an example embodiment to a pulse signal using the aforementioned voltage distribution time constant circuit, filter-and-amplifier, Schmitt trigger, and the like.

When the biosignal, for example, a heart rate signal, a pulse signal, etc., output based on the ECG sensor and the PPG sensor is converted to the pulse signal, a further reliable analysis result may be acquired.

When the biosignal is converted to the pulse signal, a separate ADC is not required and a configuration of a circuit is simplified. Accordingly, the biosignal analysis apparatus may be configured to have a low power consumption and a low area.

Referring to FIG. 9B, when converting a biosignal to a pulse signal, unpredicted noise may occur. According to an example embodiment, noise may be removed in the pulse signal based on predicted characteristic information of the pulse signal, for example, an iterative generation time or a generation interval of the pulse signal and a width of the pulse signal. For example, all of signals occurring within a threshold time after the pulse signal is generated may be regarded as noise signals and thereby ignored. Also, a pulse signal generated after the threshold time may be counted as a heart rate.

An algorithm for determining a valid pulse signal may determine a valid heart rate/valid pulse rate of a measurement target based on characteristic information of a pulse signal of the measurement target, for example, a number of times that the pulse signal is generated during a predetermined period of time, a width of the pulse signal, and the like.

Also, an algorithm for determining a valid pulse signal may estimate a time between pulse signals based on the determined valid heart rate/valid pulse rate of the measurement target, and may determine and ignore a signal generated during the estimated time between the pulse signals as a noise signal.

In addition, a biosignal analysis method according to an example embodiment may determine whether abnormality has occurred in a body of the measurement target based on a change in biometric information. For example, whether an abnormality is present in the heart of the measurement target may be determined by calculating a change speed of the heart rate of the measurement target. If the change speed of the heart rate is greater than or equal to a predetermined threshold, heart rate information, for example, a heart rate value, a change level of the heart rate, etc., of the measurement target may be stored and ECG information may be stored and managed.

That is, according to an example embodiment, a symptom of the measurement target may be diagnosed in further detail through a collective analysis algorithm associated with biometric information of the measurement target. For example, body state information of the measurement target may be generated based on heart rate information and/or ECG information that is an output value of the biosignal analysis apparatus. For example, body state information, such as a stress index, a physiological index, a psychological index, a momentum index, and the like, of the measurement target may be determined based on heart rate information and/or ECG information.

Referring to FIG. 9B, time information (hereinafter, pulse signal time information) extracted based on pulse signals, such as T1, T2, T3, T4, T5, etc., may be used to determine body state information, for example, stress, blood pressure, body fat, skin temperature, etc., of the measurement target.

For example, a body type of the measurement target may be determined based on pulse signal time information T4 and pulse signal time information T5. A sasang constitution of the measurement target, such as taeeumin, taeyangin, etc., may be diagnosed based on pulse time information, such as T1, T2, T3, T4, and T5. Further, a disease of the measurement target, such as cancer, stroke, a heart disease, etc., may be estimated.

Pulse information measured in the oriental medicine may be associated with a width size of a pulse signal. By determining whether a width of the pulse signal is greater than a threshold and by counting a pulse signal greater having a width than the threshold, it is possible to perform diagnosis based on the pulse information used in the oriental medicine. The biosignal measurement apparatus may acquire body state information of the measurement target based on a change in the width of the pulse signal, such as T4, T5, etc.

Figure 10:
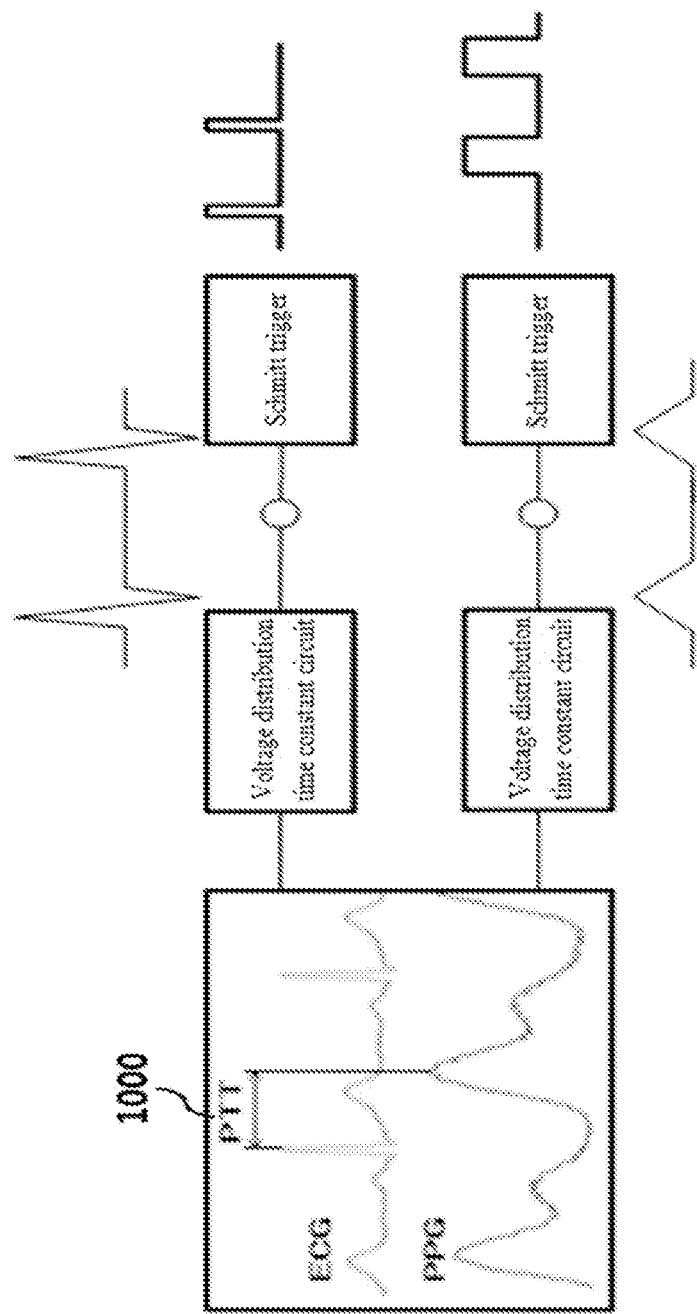
FIG. 10 illustrates an example of a method of generating pulse signal time information according to an example embodiment.

FIG. 10 illustrates an example of a method of generating pulse signal time information according to an example embodiment.

FIG. 10 illustrates a method of generating pulse signal time information T3 through measurement associated with T3 among a plurality of pieces of pulse signal time information of FIG. 9B. The pulse signal time information T3 may include information about a pulse transit time (PTT).

Referring to FIG. 10, a PTT 1000 may have a correlation with a systolic blood pressure or a diastolic blood pressure of the measurement target. The pulse signal time information T3 may be a difference value between a time at which a first peak value is measured at the biosignal measurement apparatus based on the ECG sensor and a time at which a second peak value is measured at the biosignal measurement apparatus based on the PGG sensor.

The PTT 1000 may be inverse proportional to the systolic blood pressure or the diastolic blood pressure. Accordingly, a blood pressure of the measurement target may be estimated using the PTT 1000. Although the blood pressure of the measurement target may be estimated using the PTT 1000 only, the blood pressure of the measurement target may be further accurately calculated by further using additional body information, for example, a weight, an arm length, a state of a blood vessel, etc., of the measurement target.

Figure 11:
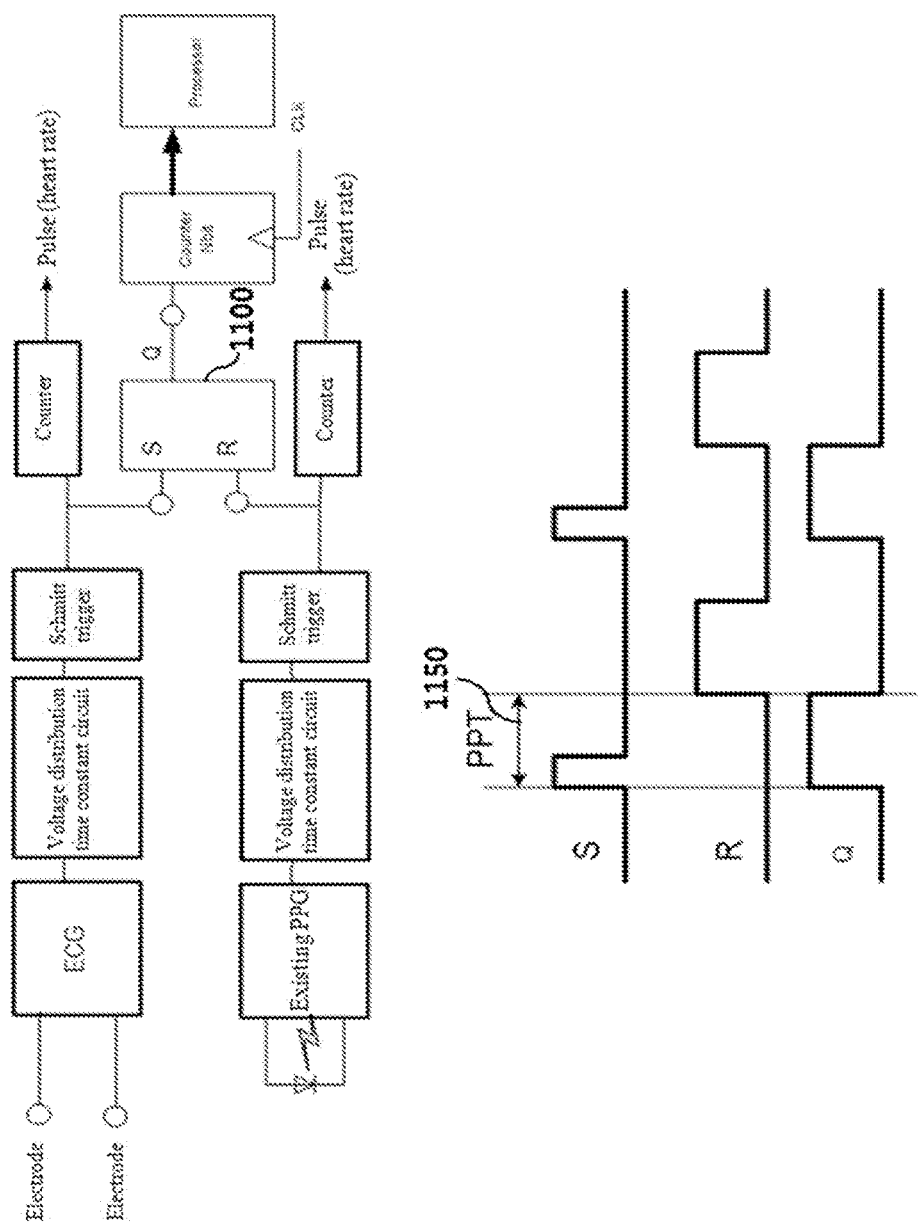
FIG. 11 illustrates an example of a biosignal measurement apparatus for measuring a biosignal of a measurement target according to an example embodiment.

FIG. 11 illustrates an example of a biosignal measurement apparatus for measuring a biosignal of a measurement target according to an example embodiment.

FIG. 11 illustrates a biosignal measurement apparatus for measuring a PTT that is included in pulse signal time information T3. For clarity of description, it is assumed that the biosignal measurement apparatus of FIG. 11 does not include a filter-and-amplifier. However, it is provided as an example only and the biosignal measurement apparatus may be configured to include the filter-and-amplifier.

Referring to FIG. 11, the biosignal measurement apparatus may measure a PPT 1150 based on a first signal that is output through a voltage distribution time constant circuit and a Schmitt trigger with respect to an ECG signal measured using an ECG sensor and a second signal that is output through the voltage distribution time constant circuit and the Schmitt trigger with respect to a pulse signal measured using a PPG sensor. A time in which a Q value is 1 based on an S-R latch circuit 1100 may be the PPT 1150.

According to an example embodiment, the biosignal measurement apparatus may simultaneously acquire a first pulse signal associated with an ECG signal and a second pulse signal associated with a pulse signal, and may generate body state information of the measurement target based on the first pulse signal and the second pulse signal. If a separate manager is present for the measurement target, body state information of the measurement target may be transmitted to the manager through a wireless/wired system. The manager may manage the measurement target based on the body state information of the measurement target.

Figure 12:
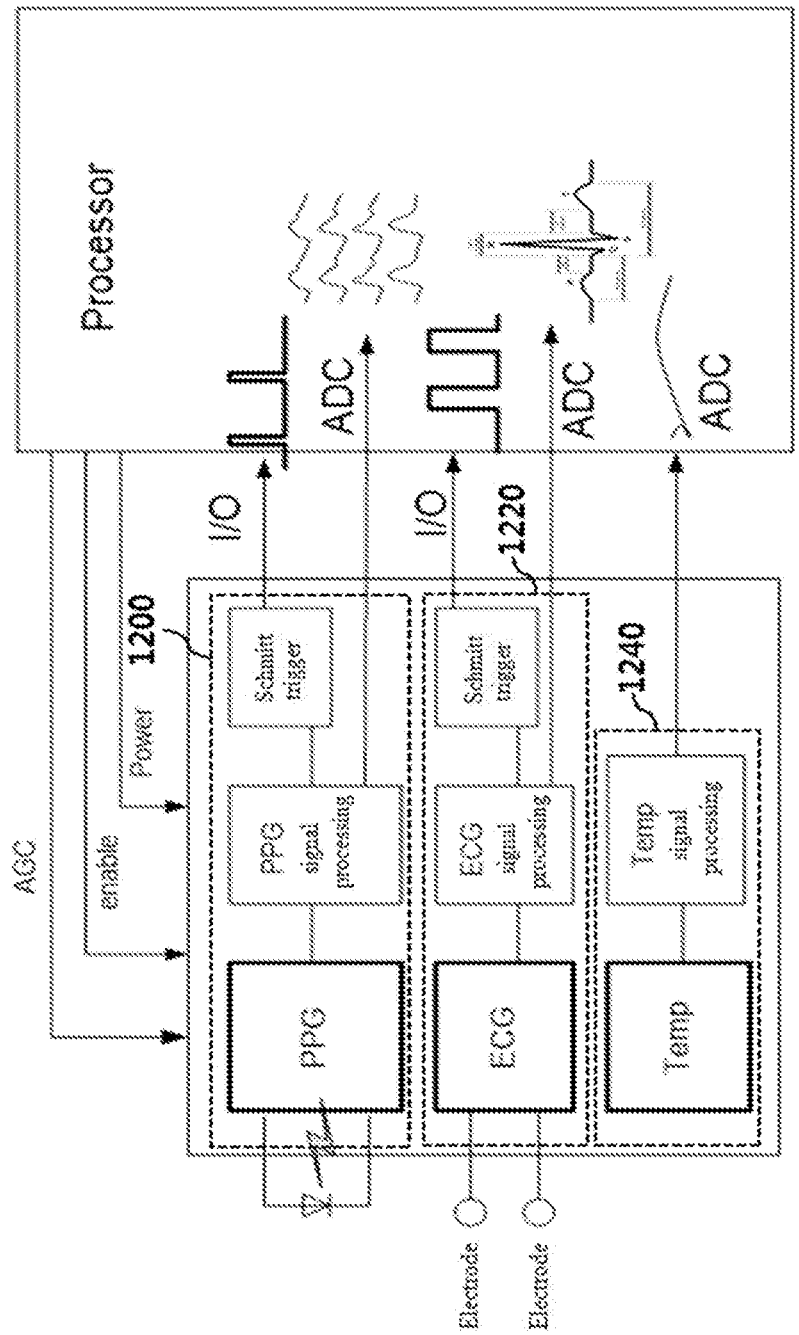
FIGS. 12 and 13 illustrate examples of a biosignal measurement apparatus for measuring a biosignal of a measurement target according to an example embodiment.
Figure 13:
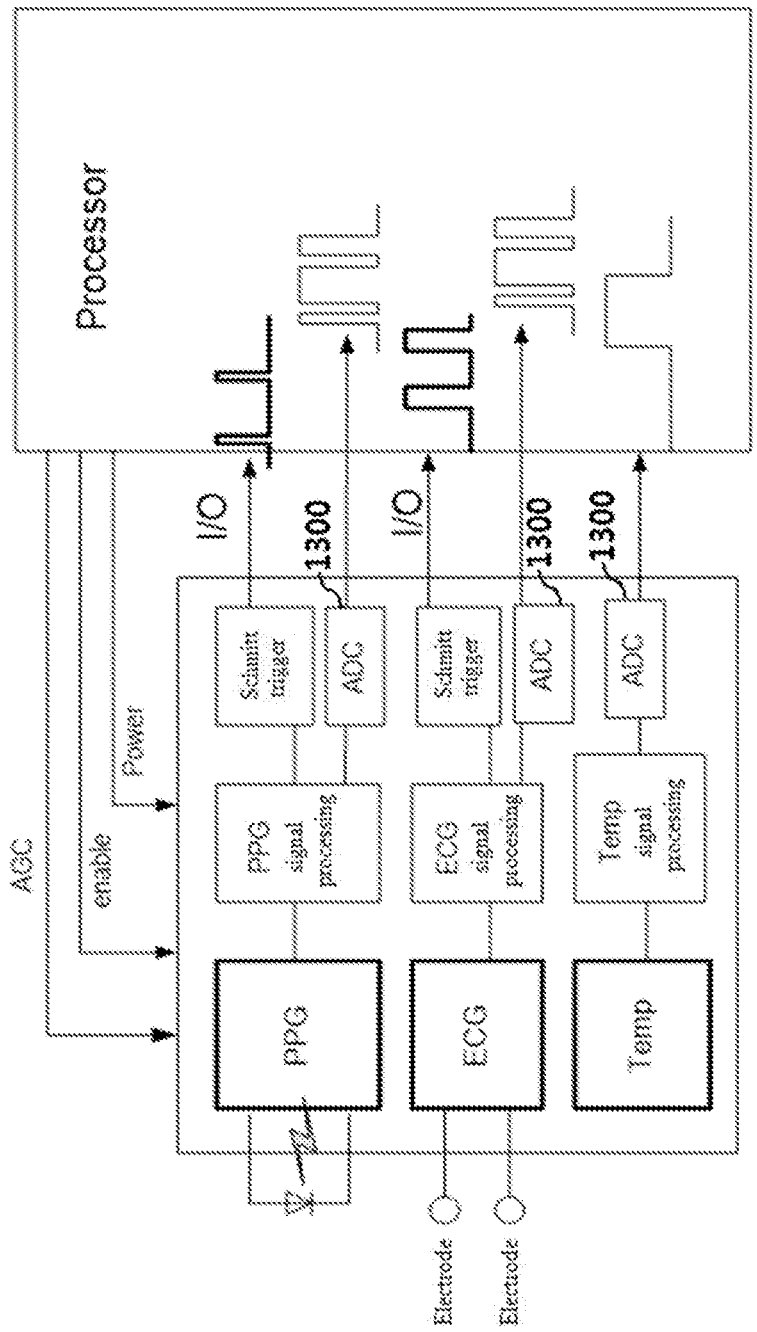

FIGS. 12 and 13 illustrate examples of a biosignal measurement apparatus for measuring a biosignal of a measurement target according to an example embodiment.

The biosignal measurement apparatus of FIG. 12 may be configured using a plurality of individual devices, for example, chips, or a single chip.

Referring to FIG. 12, the biosignal measurement apparatus may generate heart rate information, ECG information, pulse rate information, pulse waveform information, and temperature information.

As described above, when the measurement target is in a dynamic state, stable heart rate information and pulse rate information may be acquired using a voltage distribution time constant circuit configured to function as an HPF.

The biosignal measurement apparatus may include a first biosignal measurer 1200, a second biosignal measurer 1220, and a temperature measurer 1240.

The first biosignal measurer 1200 may generate pulse rate information and pulse waveform information based on the PPG-based biosignal measurement method of FIG. 6.

The second biosignal measurer 1220 may generate heart rate information and ECG information based on the ECG-based biosignal measurement method of FIG. 2.

The temperature measurer 1240 may measure a body temperature of the measurement target and may generate temperature information associated with the measured body temperature.

Pulse rate information, pulse waveform information, heart rate information, ECG information, and temperature information generated at the biosignal measurement apparatus may be stored in a memory. If at least one of the pulse rate information, pulse waveform information, heart rate information, ECG information, and the temperature information has a value outside a normal range, information regarding whether abnormality has occurred in the measurement target may be transferred to the manager.

Referring to FIG. 13, according to an example embodiment, ECG information, pulse waveform information, and temperature information may be converted to digital information using an ADC 1300, and the ECG information, the pulse waveform information, and the temperature information may be output as N bits using a counter based on a pulse width modulation (PWM).

According to an example embodiment, reliable biometric information may be acquired using a complex sensor, for example, a PPG sensor, an ECG sensor, and the like. That is, since a plurality of measurement sensors is used, another sensor may act in response to an occurrence of an error in measuring biometric information. Accordingly, a stable sensing value may be acquired when measuring biometric information. According to an example embodiment, a biosignal processing apparatus for processing a biosignal, such as ECG, PPG, temperature, etc., may generate biometric information at predetermined intervals or specific time intervals. Rather than expressing a one-minute measurement result based on a minute unit to save energy, the ECG sensor and the PPG sensor may perform measurement during a predetermined period of time, may calculate the measurement result and generate the calculation result as biometric information corresponding to a one-minute.

When a state of the measurement target is recognized as a dynamic state using an accelerometer sensor, a gyro sensor, and the like, a complex sensor may compare a currently measured signal, that is, a current measurement signal and a previously measured signal, that is, a previous measurement signal, may analyze a comparison result, and may determine a reliability of the current measurement signal to acquire reliable biometric information.

If the current measurement signal is within a measurement estimate range based on the previous measurement signal, the reliability of the current measurement signal may be determined to be relatively high. Biometric information, for example, heart rate information, ECG information, pulse rate information, and pulse waveform information, may be generated based on the current measurement signal.

Conversely, if the current measurement signal is outside the measurement estimate range based on the previous measurement signal, the reliability of the current measurement signal may be determined to be relatively low. If the reliability of the current measurement signal is low, biometric information based on the current measurement signal may not be generated. Measurement estimation information generated based on a previous measurement result may be used as biometric information of the measurement target. The measurement estimation information generated based on the previous measurement result may be determined based on a variation level in the existing biometric information. For example, if heart rate information shows an increase in a heart rate, measurement estimation information based on the previous measurement result may be generated by considering an increase level of a heart rate.

Figure 14:
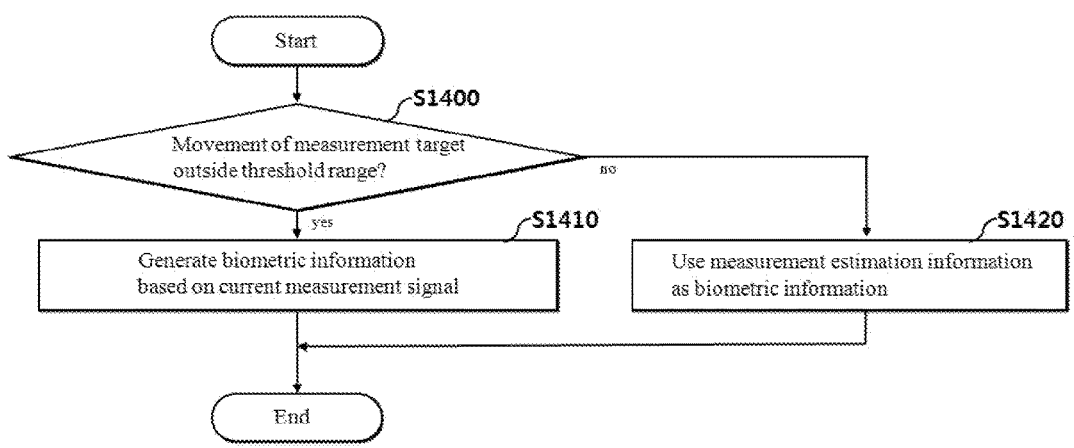
FIG. 14 is a flowchart illustrating an example of a biosignal measurement method performed at a biosignal measurement apparatus according to an example embodiment.

FIG. 14 is a flowchart illustrating an example of a biosignal measurement method performed at a biosignal measurement apparatus according to an example embodiment.

FIG. 14 illustrates a method of performing a highly reliable biosignal measurement by comparing a current measurement signal and a measurement estimate.

Referring to FIG. 14, in operation S1400, whether a movement of a measurement target is outside a threshold range may be determined.

When the movement of the measurement target is determined to be within the threshold range, a reliability of the current measurement signal may be determined to be relatively high. Accordingly, when the movement of the measurement target is determined to be within the threshold range, biometric information, for example, heart rate information, ECG information, pulse rate information, pulse waveform information, etc., may be generated based on the current measurement signal in operation S1410.

Conversely, when the movement of the measurement target is determined to be outside the threshold range, the reliability of the current measurement signal may be determined to be relatively low. Accordingly, when the movement of the measurement target is determined to be outside the threshold range, measurement estimation information generated based on the previous measurement result may be used as biometric information of the measurement target in operation S1420.

As described above, the biosignal measurement method according to the example embodiments may be configured using an application or in a form of program instructions executable through a variety of computer devices, and recorded in non-transitory computer-readable medium. The non-transitory computer-readable media may also include, alone in combination with the program instructions, data files, data structures, and the like. The program instructions recorded on the media may be those specially designed and constructed for the purposes of example embodiments, or they may be of the kind well-known and available to those having skilled in the computer software arts. Examples of non-transitory computer-readable media include magnetic media such as hard disks, floppy disks, and magnetic tape; optical media such as CD-ROM and DVDs; magneto-optical media such as floptical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific example embodiments, it will be apparent to one of ordinary skill in the art that various alterations and modifications in form and details may be made in these example embodiments without departing from the spirit and scope of the claims and their equivalent. Therefore, the scope of the disclosure is defined not by the detailed description, but by the claims and their equivalents, and all variations within the scope of the claims and their equivalents are to be construed as being included in the disclosure

What is claimed is:

1. A method of measuring a biosignal, the method comprising:
   measuring, at a biosignal measurement apparatus, a biosignal using a biosignal measurement sensor;
   processing, at the biosignal measurement apparatus, the biosignal and converting the biosignal to a pulse signal using a first voltage distribution time constant circuit and a waveform converter; and
   counting, at the biosignal measurement apparatus, the pulse signal using a counter and generating first biometric information,
   wherein the first voltage distribution time constant circuit filters a signal of a specific frequency band from the biosignal based on voltage distribution using a series resistance included in the first voltage distribution time constant circuit.

2. The method of claim 1, wherein the converting of the biosignal to the pulse signal comprises:
   generating, at the biosignal measurement apparatus, the biosignal as a first wave signal using the first voltage distribution time constant circuit; and
   converting, at the biosignal measurement apparatus, the first wave signal to the pulse signal using the waveform converter,
   wherein the first voltage distribution time constant circuit comprises a first series resistance and a second series resistance provided between a power voltage and a ground and configured to distribute the power voltage, and a first capacitor connected between the first series resistance and the second series resistance, and
   wherein the first voltage distribution time constant circuit has a voltage distribution time constant of a first threshold or less that is determined using the first series resistance, the second series resistance, and the first capacitor.

3. The method of claim 1, wherein the converting of the biosignal to the pulse signal comprises:
   generating, at the biosignal measurement apparatus, the biosignal as a first wave signal using the first voltage distribution time constant circuit;
   filtering, at the biosignal measurement apparatus, and/or amplifying the first wave signal using a filter-and-amplifier, and acquiring the filtered first wave signal; and
   converting, at the biosignal measurement apparatus, the filtered first wave signal to the pulse signal using the waveform converter,
   wherein the first voltage distribution time constant circuit comprises a first series resistance and a second series resistance provided between a power voltage and a ground and configured to distribute the power voltage, and a first capacitor connected between the first series resistance and the second series resistance, and
   wherein the first voltage distribution time constant circuit has a voltage distribution time constant of a first threshold or less that is determined using the first series resistance, the second series resistance, and the first capacitor.

4. The method of claim 1, further comprising:
   generating, at the biosignal measurement apparatus, the biosignal as a second wave signal using a second voltage distribution time constant circuit;
   converting, at the biosignal measurement apparatus, the second wave signal to a digital signal using an analog-to-digital converter (ADC); and
   generating, at the biosignal measurement apparatus, second biometric information based on the digital signal.

5. The method of claim 4, wherein the first voltage distribution time constant circuit comprises a first series resistance and a second series resistance provided between a first power voltage and a ground and configured to distribute the first power voltage, and a first capacitor connected between the first series resistance and the second series resistance,
   wherein the first voltage distribution time constant circuit has a voltage distribution time constant of a first threshold or less that is determined using the first series resistance, the second series resistance, and the first capacitor,
   wherein the second voltage distribution time constant circuit comprises a third series resistance and a fourth series resistance provided between a second power voltage and a ground, and configured to distribute the second power voltage, and a second capacitor connected between the third series resistance and the fourth series resistance, and
   wherein the second voltage distribution time constant circuit has a voltage distribution time constant of a second threshold or more that is determined using the third series resistance, the fourth series resistance, and the second capacitor.

6. The method of claim 5, further comprising:
removing, at the biosignal measurement apparatus, noise in the pulse signal based on a characteristic of the pulse signal;
determining, at the biosignal measurement apparatus, a reliability of the biometric information based on comparison between a measurement estimate that is estimated based on previously generated biometric information and the biometric information; and
applying, at the biosignal measurement apparatus, the measurement estimate or the biometric information to generate body state information of a measurement target based on the reliability.

7. A biosignal measurement apparatus comprising:
a processor,
wherein the processor is configured to
measure a biosignal using a biosignal measurement sensor,
process the biosignal and convert the biosignal to a pulse signal using a first voltage distribution time constant circuit and a waveform converter, and
count the pulse signal using a counter and generate first biometric information, and
wherein he first voltage distribution time constant circuit filters a signal of a specific frequency band from the biosignal based on voltage distribution using a series resistance included in the first voltage distribution time constant circuit.

8. The biosignal measurement apparatus of claim 7, wherein the processor is configured to
generate the biosignal as a first wave signal using the first voltage distribution time constant circuit, and
convert the first wave signal to the pulse signal using the waveform converter,
wherein the first voltage distribution time constant circuit comprises a first series resistance and a second series resistance provided between a power voltage and a ground and configured to distribute the power voltage, and a first capacitor connected between the first series resistance and the second series resistance, and
wherein the first voltage distribution time constant circuit has a voltage distribution time constant of a first threshold or less that is determined using the first series resistance, the second series resistance, and the first capacitor.

9. The biosignal measurement apparatus of claim 8, wherein the processor is configured to
generate the biosignal as a first wave signal using the first voltage distribution time constant circuit,
filter and/or amplify the first wave signal using a filter-and-amplifier, and
acquire the filtered first wave signal, and to convert the filtered first wave signal to the pulse signal using the waveform converter, wherein the first voltage distribution time constant circuit comprises a first series resistance and a second series resistance provided between a power voltage and a ground and configured to distribute the power voltage, and a first capacitor connected between the first series resistance and the second series resistance, and
wherein the first voltage distribution time constant circuit has a voltage distribution time constant of a first threshold or less that is determined using the first series resistance, the second series resistance, and the first capacitor.

10. The biosignal measurement apparatus of claim 7, wherein the processor is configured to
generate the biosignal as a second wave signal using a second voltage distribution time constant circuit,
convert the second wave signal to a digital signal using an analog-to-digital converter (ADC), and
generate second biometric information based on the digital signal.

11. The biosignal measurement apparatus of claim 10, wherein the first voltage distribution time constant circuit comprises a first series resistance and a second series resistance provided between a first power voltage and a ground and configured to distribute the first power voltage, and a first capacitor connected between the first series resistance and the second series resistance,
wherein the first voltage distribution time constant circuit has a voltage distribution time constant of a first threshold or less that is determined using the first series resistance, the second series resistance, and the first capacitor,
wherein the second voltage distribution time constant circuit comprises a third series resistance and a fourth series resistance provided between a second power voltage and a ground, and configured to distribute the second power voltage, and a second capacitor connected between the third series resistance and the fourth series resistance, and
wherein the second voltage distribution time constant circuit may have a voltage distribution time constant of a second threshold or more that is determined using the third series resistance, the fourth series resistance, and the second capacitor.

12. The biosignal measurement apparatus of claim 11, wherein the processor is configured to
remove noise in the pulse signal based on a characteristic of the pulse signal,
determine reliability of the biometric information based on comparison between a measurement estimate that is estimated based on previously generated biometric information and the biometric information, and
apply the measurement estimate or the biometric information to generate body state information of a measurement target based on the reliability.

* * * * *